United States Patent [19]

Hsieh et al.

[11] Patent Number: 4,535,059

[45] Date of Patent: Aug. 13, 1985

[54] MUCONIC ACID PRODUCTIVITY BY A STABILIZED MUTANT MICROORGANISM POPULATION

[75] Inventors: Jih-Han Hsieh, Parsippany; Sol J. Barer, Fanwood; Peter C. Maxwell, New Providence, all of N.J.

[73] Assignee: Celanese Corporation, New York, N.Y.

[21] Appl. No.: 457,807

[22] Filed: Jan. 13, 1983

[51] Int. Cl.³ .................. C12P 7/40; C12P 7/44; C12N 9/02; C12N 9/04; C12N 1/26; C12N 1/20; C12N 1/28; C12M 1/36
[52] U.S. Cl. ............................. 435/142; 435/136; 435/189; 435/190; 435/245; 435/248; 435/253; 435/249; 435/289; 435/291; 435/813; 435/877
[58] Field of Search ............... 435/136, 142, 189, 190, 435/245, 248, 249, 253, 289, 291, 813, 877

[56] References Cited

U.S. PATENT DOCUMENTS

| | | | |
|---|---|---|---|
| 2,686,754 | 8/1954 | Monod | 435/813 |
| 2,822,319 | 2/1958 | Monod | 435/813 |
| 4,167,450 | 9/1979 | Chesbro et al. | 435/813 |
| 4,355,107 | 10/1982 | Maxwell | 435/253 |
| 4,399,220 | 8/1983 | Smiley | 435/139 |

*Primary Examiner*—Thomas G. Wiseman
*Assistant Examiner*—Robin Lyn Teskin
*Attorney, Agent, or Firm*—Depaoli & O'Brien

[57] ABSTRACT

This invention provides an improved fermentation process for bioconversion of toluene to muconic acid.

The process involves operating the bioconversion system under phosphate-limiting conditions so as to achieve an increase in specific muconic acid productivity with a stabilized population of microorganism such as an ATCC No. 31,916 type of *Pseudomonas putida* Biotype A mutant strain.

5 Claims, 1 Drawing Figure

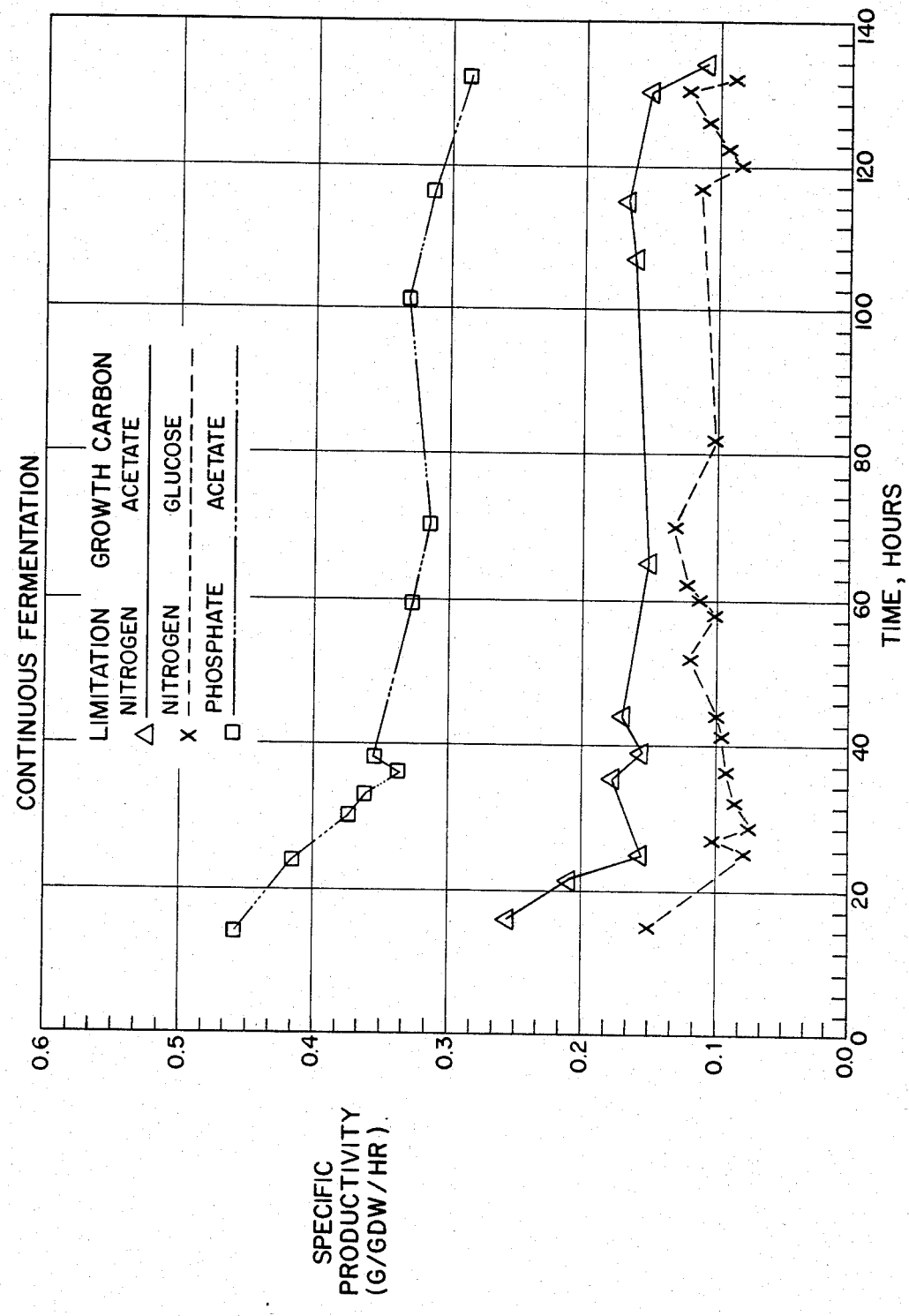
Figure

MUCONIC ACID PRODUCTIVITY BY A STABILIZED MUTANT MICROORGANISM POPULATION

BACKGROUND OF THE INVENTION

Microorganisms adapt to a broad variety of environmental conditions. This versatility is characterized by the reorganization of macromolecular structure, the induction and/or suppression of enzyme systems, and the redistribution among cellular metabolic pools.

The theory and practice of "nutrient limitation" effects in fermentation systems is elaborated in literature such as Biochemical Engineering, Second Edition, Academic Press, New York, 1973; Biochemical Engineering Fundamentals, McGraw-Hill, New York, 1977; Principles Of Microbe And Cell Cultivation, John Wiley and Sons, New York, 1975; Fermentation And Enzyme Technology, John Wiley and Sons, New York, 1979; and the like.

Biotechnology and Bioengineering, 18, 180 (1976) is directed to transient response of *Enterobacter aerogenes* under a dual nutrient limitation in a chemostat. Quantitative evidence is provided that cells can be grown under dual nutrient limitation. The pattern of response is consistent with the hypothesis, for example, that phosphate-limitation restricts nucleic acid synthesis and that nitrogen-limitation restricts protein synthesis.

In a continuous fermentation (or chemostat) mode of cultivating microorganisms, growth nutrient-limitation is necessary in order to achieve a "steady state", i.e., a constant level of cell concentration in a continuous flow reactor with a defined medium concentration.

As indicated in the literature, conventional nutrient-limitation is primarily a technique to achieve steady state continuous fermentation and to study various yield and maintenance factors of cell mass with respect to various nutrients for cell growth. For the production of conventional fermentation products, such as ethanol, citric acid, lactic acid, acetic acid, and the like (primary metabolites), or antibiotics, microbial toxins, and the like (secondary metabolites) in a continuous flow reactor, nutrient-limitation can also be used to achieve steady state product formation. However, in a chemostat this type of nutrient-limitation has little or no effect on the stability of cells, i.e., the maintenance of the production and productivity level of a specific metabolite.

With a *Pseudomonas putida* type of mutant strain, the cells can grow on a preferred growth carbon and energy source (glucose, succinate or acetate) and convert a non-growth carbon source (e.g., toluene) to a product (e.g., muconic acid). The mutant strain at least initially is unable to grow on toluene as a carbon source. However, in the presence of toluene and other nutrients over a prolonged period of time (1-2 days), cells within the population "revert"; i.e., exhibit a parent strain ability to grow on toluene. Initially only a few cells revert, perhaps only a single cell, and eventually the reverted cell(s) grow and become the dominant cell type because of the selective ability to grow on both the growth carbon and the "non-growth" carbon sources that are present. This reversion problem is unique for genetically manipulated mutant microorganisms in bioconversion systems.

In addition to achievement of a stable population of a mutant microorganism for the production of a specific metabolite in a bioconversion system, it is desirable to establish and maintain a high productivity level of the specific metabolite.

Accordingly, it is an object of this invention to provide an improved fermentation process in which a population of a mutant microorganism is stabilized by suppression of cell reversion, and the specific productivity of an accumulating quantity of specific metabolite is increased.

It is another object of this invention to provide an improved fermentation process for bioconversion of toluene to accumulating muconic acid with increased specific productivity in a steady state continuous mode.

Other objects and advantages of the present invention shall become apparent from the accompanying description and examples.

DESCRIPTION OF THE INVENTION

One or more objects of the present invention are accomplished by the provision of an improved fermentation process for production of an accumulating quantity of muconic acid by bioconversion of a non-growth toluene carbon source with a homogeneous population of a mutant microorganism, the improvement which comprises limiting the presence of essential phosphate nutrient within a phosphate:growth carbon weight ratio range between about 0.04-0.08:1 in the aqueous fermentation medium which is maintained at a pH between about 5-8, thereby (1) increasing the specific muconic acid productivity of the microorganism, and (2) stabilizing the microorganism population whereby cell reversion is suppressed, wherein said suppressed cell reversion is to a parent strain of the microorganism which has the ability to grow on the said non-growth toluene carbon source.

The results obtained with controlled phosphate-limitation within a narrow range of phosphate:growth carbon weight ratio are unique in that two important advantages are achieved, i.e., an increase in specific muconic acid productivity, and stabilization of the mutant microorganism population.

If instead the nutrient limitation effected is a nitrogen-limitation in the bioconversion system, then stabilization of the mutant microorganism is achieved, but the specific productivity of muconic acid is at a much lower level than with phosphate-limitation, as demonstrated in the FIGURE.

In accordance with the present invention process improvement, with phosphate-limited conditions the specific productivity rate is about 0.3-0.6 grams of muconic acid per gram of dry cell weight per hour in a continuous fermentation mode. The muconic acid accumulates in the aqueous fermentation medium to a concentration level about about 12 grams per liter.

Another critical factor in establishing and maintaining a high specific muconic acid productivity level is the control of pH conditions in the aqueous fermentation medium. Optimal muconic acid productivity is realized only when the pH is in a range between about 5-8, and preferably within a pH range between about 6.5-7.5. The addition of acid or base is employed as appropriate to control the pH within the desired range.

The term "nutrient" as employed herein refers to elemental nutrients essential for cell growth in an aqueous fermentation medium, such as nitrogen, phosphorus, sulfur, magnesium, iron, calcium, zinc, sodium, copper, molybdenum, manganese, potassium, sodium, and the like. "Growth carbon" is an essential element which is excluded from the term "nutrient" for purposes of the present invention, and it is understood that growth carbon is always present in the dynamic bioconversion systems of interest.

The term "non-growth carbon" refers to a carbon source which a mutant microorganism does not metabolize for cell growth. For purposes of the present invention process, toluene is employed as the non-growth carbon source.

The term "reversion" as noted previously refers to the phenomenon in which a homogeneous mutant microorganism population regains a parent strain ability to grow on a non-growth carbon source in a bioconversion system. The reversion mechanism appears to involve an increasing accumulation of a "contaminant" microorganism on the basis of a selective growth advantage provided by a specific nutrient environment. The application of phosphate-limitation to suppress this reversion phenomenon in present invention bioconversion systems is novel, and the concomitant increase in specific muconic acid productivity is an important additional advantage of the process improvement described herein.

Under phosphate-limited conditions the cell growth is restricted, with the result that the cells selectively grow on a preferred carbon source, such as glucose, succinate or acetate, instead of growing on the non-growth toluene carbon source. Consequently, the stability of a reversion-susceptible mutant strain population is improved. This growth state can be found in continuous fermentation (chemostat) and in the early stage of fed-batch fermentation.

For resting or non-growing cells under phosphate limitation, a present invention mutant strain, after proper induction to induce enzymes and in the absence of growth nutrient, converts the non-growth toluene carbon source to extracellular accumulating muconic acid and obtains energy from the reaction for cell maintenance, and consequently achieves cell stability. This situation can be found in the stationary growth phase (or later period) of a fed-batch fermentation, and in the concentrated cells of a continuous fermentation with cell recycle.

The present invention improved method of increasing muconic acid productivity with a stabilized population of a mutant microorganism is generally applicable to constructed strains which are capable of metabolizing non-growth carbon sources to metabolites other than carbon dioxide and/or biomass. Such strains are derived from naturally occurring organisms such as the species *Pseudomonas putida, Pseudomonas aeruginosa, Pseudomonas fluorescens;* some members of the genera Nocardia; various unclassified fungi (both molds and yeasts); and the like, excluding nitrogen-fixing species.

In the following description the literature is particularly selected from reference to metabolism of a toluene substrate to muconic acid which is recoverable as a useful product.

In the Journal Of Bacteriology, 134, 756 (1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through $\beta$-ketoadipate to biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed $\beta$-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No naturally occurring microorganisms (e.g., *Pseudomonas putida*) are known that metabolize an aromatic hydrocarbon substrate such as toluene by the ortho pathway via muconic acid and $\beta$-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation.

This type of mutant strain can be provided by a process for microorganism construction which comprises (1) culturing microorganism species selectively to provide strain A1 which metabolizes toluene by the ortho pathway via catechol to muconic acid, and which subsequently metabolizes the resultant muconic acid via $\beta$-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

Microorganisms constructed in the manner outlined above are described in U.S. Pat. No. 4,355,107 (incorporated by reference). These mutants possess a novel combination of enzymes which include (1) dihydrodihydroxybenzoate dehydrogenase enzyme; and (2) catechol 1,2-oxygenase enzyme with activity that is not inhibited in the presence of less than about five gram/liter of muconic acid in a growth medium.

Illustrative of these mutant microorganisms are constructed strains of fluorescent Pseudomonads each of which has the following characteristics:
(a) possesses catechol 1,2-oxygenase enzyme with activity that is not inhibited in the presence of a low level of muconic acid in a growth medium;
(b) lacks substantially catechol 2,3-oxygenase enzyme;
(c) lacks functional muconate lactonizing enzyme;
(d) cells are rod shaped, vigorously motile and polarly flagellated; and
(e) cells grow well on p-hydroxybenzoate.

A specific mutant microorganism of the type described above is ATCC No. 31,916 strain of *Pseudomonas putida* Biotype A.

Employing one of the constructed microorganisms described above in the invention process for the production of muconic acid from toluene, under continuous fermentation conditions the rate of toluene conversion typically is about 0.32 gram of muconic acid produced per gram of dry cell weight per hour. In a fed-batch fermentation mode a specific productivity up to 1.4 grams of muconic acid per gram of dry cell weight per hour is obtained. The conversion of toluene proceeds readily at a dry weight cell concentration of 1–3 grams per liter, with a resultant muconic acid production rate of 0.4–2 grams per liter per hour. Under optimal conditions, the muconic acid accumulation limit can approach up to about 50 grams of muconic acid per liter of growth medium. The bioconversion normally is conducted at ambient temperatures up to about 31° C.

As described in the Examples and as summarized in the FIGURE, continuous production of muconic acid from toluene has been demonstrated in a chemostat using a mutant strain of *Pseudomonas putida*.

The production of muconic acid from toluene is sensitive to the level of growth carbon (catabolite repression), phosphate-nutrient concentration (i.e., cell stability and specific muconic acid productivity level), muconic acid concentration (end product inhibition and repression) and toluene level and mass transfer rate to the fermentation broth (enzyme induction and growth inhibition).

It has been found that in order to achieve higher reactor productivity for muconic acid production the excess energy generated by the bioconversion needs to be removed. During a continuous fermentation with cell recycle, a minimal amount of growth carbon and other nutrients is required for maintenance, and for growth as an energy sink to remove the excess energy generated.

Another significant advantage of the present invention improved process is an economic one, as derived from the low phosphate nutrient input into the bioconversion system.

The following examples are further illustrative of the present invention. The components and specific ingredients are presented as being typical, and various modifications can be derived in view of the foregoing disclosure within the scope of the invention.

For cultivation, carbon sources such as glucose, succinate and acetate are added aseptically prior to inoculation. Incubation conditions are in 250 ml shake flasks. Shaking is in a rotary shaker with temperature controlled at 28° C.

Microbial growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophotometer.

Cultures are stored under liquid nitrogen.

EXAMPLE I

This Example illustrates the construction of a strain of microorganism which oxidizes toluene via the ortho ($\beta$-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluene can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31,916 type of mutant strain.

Strain MW 1210 of Example I is subjected to continuous cultivation with toluene as the sole source of carbon. Initially a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5mM p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5mM succinate and 5.0mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

EXAMPLE III

This Example illustrates the stabilization of a population of a mutant microorganism by means of phosphate-limitation, and further illustrates the increase in specific muconic acid productivity that is achieved by phosphate-limitation in accordance with the invention process.

Microorganism

The microorganism employed is a *Pseudomonas putida* Biotype A mutant strain (ATCC 31,916) as described in Example II. The microorganism contains enzymes which enable catabolism of toluene, and enzymatic blocks are present in this pathway which allow accumulation of muconic acid rather than further oxidation to carbon dioxide and/or biomass.

Fermentation Media

Typical fermentation media are listed in the TABLE. The media are prepared by adding appropriate growth carbon source in deionized water and sterilized in an autoclave (Barnstead sterilizer, Sybron Co.) for at least 30 minutes at 121° C. and 15 psig.

For continuous fermentation systems, the fresh feed medium is prepared by adding $Na_2HPO_4$, $KH_2PO_4$ and $FeSO_4.7H_2O$ to a 14 liter Pyrex glass carboy, and sterilizing $(NH_4)_2SO_4$, $MgSO_4.7H_2O$ and $CaCl_2$ separately in a 1000 ml flask with 50 ml deionized water.

Glacial acetic acid as a growth carbon source (Medium AN-1 and LP-1) is sterilized separately in a 1000 ml flask with 500 ml deionized water. The acetic acid concentration in the feed is 3.5 g/l in most cases. These media are sterilized and cooled before aseptic mixing to prevent precipitation. The pH of the 12 liter medium is adjusted from 4.0 to 5.4 by adding 70 cc of 5N NaOH or KOH solution. Glucose (Medium GN-1) as a growth carbon source is also sterilized separately to prevent caramelization, and aseptically combined with the rest of the medium. During a continuous fermentation, the pH of the medium is controlled at 6.9 with 3M $NH_4OH$ and 1M $H_2SO_4$ solutions.

For fed-batch fermentation systems, the medium is sterilized in a 16 liter Microgen fermentor containing 12 liters of LP-1 medium with 20mM of sodium acetate as growth carbon to start fermentation. After sterilization, the medium pH is adjusted to 6.9 with 5N NaOH or KOH solution. Additional acetic acid and phosphate is continuously added during the fermentation. The pH of the medium is controlled at 6.9 with 10M $NH_4OH$ and 1M $H_2SO_4$ solutions.

Inoculum Preparation

The *P. putida* mutant strain culture (regular "NO" medium aqueous culture in polypropylene culture vial stored in liquid nitrogen) is thawed and transferred (1–1.5 ml) to 250 ml shake flasks containing 50 ml of regular "NO" medium with 20mM sodium succinate as growth carbon source and incubated at 30° C., 250 RPM for 20 to 24 hours to a turbidity of 200–240 klett units. The shake flasks are inoculated aseptically to the fermentors. Fifty ml inoculum (one flask) is used to inoculate a 2-liter Bioflow fermentor and 150 ml inoculum (three flasks) to inoculate a 16-liter Microgen fermentor.

Fed-Batch Fermentation

Fed-batch fermentation experiments are conducted in a Microgen 16-liter fermentor containing 12 liters LP-1 medium with 20mM of sodium acetate to start fermentation. One hundred and fifty ml of the prepared inoculum is used to inoculate the Microgen fermentor. After the inoculation, toluene is supplied to the fermentation medium in vapor phase via air stripping at an air toluene vapor flow rate of 125 cc/min. The fermentation temperature is controlled at 30° C., pH at 6.9 with 10M $NH_4OH$ and 1M $H_2SO_4$ solutions, dissolved oxygen at 30–90% saturation with 600 RPM agitation and 5 liter/min aeration (or approximately 0.5 VVM). Pluronic L61 polyol (BASF) was used as an antifoam agent.

As the turbidity of the fermentation medium reaches 90–110 klett units (about 9–15 hours after inoculation), an aqueous solution containing 10 wt% acetic acid, 0.114 wt% $Na_2HPO_4$ and 0.218 wt% $KH_2PO_4$ is added to the fermentor medium at a rate of 0.4 ml/min. The air-toluene vapor rate is increased to 250 cc/min and then increased to 500 cc/min as the broth turbidity reaches 250 klett units. The air-toluene vapor rate is eventually increased to 750 cc/min as the turbidity reaches 450–550 klett units and a muconic acid product concentration of 15 g/l is achieved.

The fed-batch mode of fermentation is normally continued for 24–36 hours. The culture broth is then filtered to remove cells with a Romicon ® hollow tube "cross-flow" ultrafilter which has a polysulfone type ultrafiltration membrane (PM-100, molecular weight cutoff 100,000). The clear cell-free filtrate is adjusted to pH 1–1.5 with concentrated $H_2SO_4$. The precipitated muconic acid is filtered, washed, dried and recovered as a white solid.

A maximum specific productivity of 1.4 g/gdw/hr is achieved during the fermentation. The fermentation is conducted by restricting the cell growth throughout the batch fermentation cycle. During the early phase of fermentation (i.e., 6–12 hours after inoculation of cells), the growth carbon source (20mM or 1.2 g/l acetate) and total phosphate (3mM) are in excess to initiate the growth of cells from 0.5–1.0 klett unit (after inoculation) to 50–100 klett units with 1–2mM muconic acid concentration with utilization of the growth carbon source and the phosphate. At this point, growth carbon source as well as the required phosphate level are fed to the fermentor to provide additional growth and enzyme induction.

During this period of fermentation, both the cell growth and enzyme induction proceed simultaneously. However, because of the difference in the supply of acetate and/or phosphate and the rate of consumption by the organism, the fermentation gradually converts from a growth carbon-limited fermentation (favoring enzyme induction and reducing catabolite repression) to a phosphate-limited fermentation (energetically favored product formation and reduction in cell reversion).

Besides the interrelationship between enzyme induction, catabolite repression, energy and maintenance requirements and product inhibition, the most important process variable is the mass transfer of toluene to the fermentation broth in relation to the microorganism concentration. Too little or too much toluene concentration in each of the cell growth, enzyme induction and product formation stages results in reduced biocatalytic activity, lower product concentration and lower reactor productivity.

Continuous Fermentation

To start a continuous fermentation operation, a 2-liter Bioflow fermentor with 1.5 liters growth medium (LP-1 medium with 3.5–3.9 g/l acetic acid) is inoculated with 50 ml of prepared inoculum to run batchwise initially. The fermentation temperature is controlled at 30° C., pH at 6.9 with 3M $NH_4OH$ and 1M $H_2SO_4$ solutions, dissolved oxygen at 30–90% saturation with 500–600 RPM agitation and 0.75–1.25 liter/min aeration (approximately 0.5–0.83 VVM, volume of air/volume of fermentation broth/min). The air-toluene vapor rate is maintained at 20 cc/min (or 0.014 VVM). VVM is defined as the volume of gas under ambient condition/volume of working volume/min.

As the turbidity of the fermentation broth reaches 60–90 klett units which is equivalent to 0.21–0.32 g/l cell concentration (about 9–16 hours after inoculation), the feed pump is activated. Calibrated at a desired rate, the liquid broth level in the fermentor is maintained via overflow of the broth to a sterilized receiving tank thus achieving a constant inlet and outlet flow rate. The air-toluene vapor rate is increased to 75 cc/min (or 0.05 VVM) and the continuous fermentation is started.

BRIEF DESCRIPTION OF FIGURE

The FIGURE is a summary of continuous fermentation operations conducted at a dilution rate of 0.18 $hr^{-1}$. Time zero shown in the FIGURE is the beginning of continuous fermentation. After 4–6 residence times; i.e., 20 to 30 hours of continuous fermentation, the fermentations reach steady state as evidenced by a constant specific muconic acid productivity by the cells. The specific productivity (biocatalyst activity) is defined as: (muconic acid concentration/cell concentration) times dilution rate in terms of grams of muconic acid per gram dry cell weight per hour (g/gdw/hr).

As shown in the FIGURE, the biocatalyst activity (specific productivity) under phosphate-limitation is about 3–4 fold higher than that obtained under nitrogen-limited fermentation with glucose as the carbon source, and about two fold higher than that with acetate as the carbon source under nitrogen-limitation.

TABLE

| Chemicals (g/l) | FERMENTATION MEDIA | | | | |
|---|---|---|---|---|---|
| | Regular "NO" Medium | Modified "NO" Medium | GN-1 Medium | AN-1 Medium | LP-1 Medium |
| $Na_2HPO_4$ | 7.1 | 7.1 | 7.1 | 7.1 | 0.0426 |
| $KH_2PO_4$ | 13.6 | 13.6 | 13.6 | 13.6 | 0.0817 |
| $(NH_4)_2SO_4$ | 2.25 | 2.25 | 1.12 | 0.281 | 1.12 |
| $MgSO_4.7H_2O$ | 0.246 | 0.738 | 0.738 | 0.738 | 0.738 |
| $CaCl_2.2H_2O$ | 0.0147 | 0.0294 | 0.0294 | 0.0294 | 0.0294 |
| $FeSO_4.7H_2O$ | 0.00278 | 0.00834 | 0.0167 | 0.0167 | 0.0167 |
| Glucose | — | — | 8.0 | — | — |
| Acetic Acid | — | — | — | 3.0 | 3.9 |

All chemical concentrations are in g/l. Unless otherwise specified, the medium is prepared by adding appropriate growth carbon source in deionized water.

What is claimed is:

1. In a fermentation process for the production of muconic acid involving the culturing of a mutant Pseudomonad having the identifying characteristics of *Pseudomonas putida* ATCC No. 31,916 under conditions permitting the formation of muconic acid and recovery of muconic acid wherein the improvement comprises: limiting the presence of essential phosphate nutrient within a phosphate: growth carbon weight ratio range between about 0.04–0.08:1 in the aqueous fermentation medium which is maintained at a pH between about 5 to 8; thereby (1) increasing the specific muconic acid productivity of the microorganism, and (2) stabilizing the microorganism population whereby cell reversion is suppressed, wherein said suppressed cell reversion is to a parent strain of the microorganism which has the ability to grow on a non-growth toluene carbon source.

2. A fermentation process in accordance with claim 1 wherein the specific productivity rate is 0.3–0.6 grams of muconic acid per gram of dry cell weight per hour.

3. A fermentation process in accordance with claim 1 wherein the muconic acid accumulates in the aqueous fermentation medium to a concentration level above about 12 grams per liter.

4. A fermentation process in accordance with claim 1 wherein the aqueous fermentation medium contains cell growth essential nutrients comprising soluble nitrogen, calcium, magnesium, iron, potassium, and sodium compounds.

5. A fermentation process in accordance with claim 1 wherein the microorganism is *Pseudomonas putida* Biotype A mutant strain ATCC No. 31,916.

* * * * *